(12) United States Patent
Weissman et al.

(10) Patent No.: US 11,130,813 B2
(45) Date of Patent: *Sep. 28, 2021

(54) TREATMENT OF CANCER WITH DUAL TARGETING OF CD47 AND EGFR

(71) Applicant: The Board of Trustees of the Leland Stanford Junior University, Stanford, CA (US)

(72) Inventors: Irving L. Weissman, Stanford, CA (US); Stephen Willingham, Mountain View, CA (US); Doris Po Yi Ho, Daly City, CA (US); Piero D. Dalerba, New York, NY (US); Kelly Marie McKenna, Palo Alto, CA (US); Jens-Peter Volkmer, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 122 days.

This patent is subject to a terminal disclaimer.

(21) Appl. No.: 16/411,547

(22) Filed: May 14, 2019

(65) Prior Publication Data
US 2019/0322751 A1 Oct. 24, 2019

Related U.S. Application Data

(63) Continuation of application No. 15/373,150, filed on Dec. 8, 2016, now Pat. No. 10,344,094.
(Continued)

(51) Int. Cl.
*A61K 39/395* (2006.01)
*C07K 16/28* (2006.01)
(Continued)

(52) U.S. Cl.
CPC .... *C07K 16/2863* (2013.01); *A61K 39/39558* (2013.01); *A61P 35/00* (2018.01);
(Continued)

(58) Field of Classification Search
None
See application file for complete search history.

(56) References Cited

U.S. PATENT DOCUMENTS 8,728,476 B2 5/2014 Van Den Berg
9,352,037 B2 5/2016 Van Den Berg
(Continued)

FOREIGN PATENT DOCUMENTS

WO 2011/133819 A2 10/2011
WO 2014/179132 A1 11/2011
(Continued)

OTHER PUBLICATIONS

Seow et al., Advances in targeted and immunobased therapies for colorectal cancer in the genomic era, Onco Targets Ther. 9:1899-1920,2016.*
(Continued)

*Primary Examiner* — Claire Kaufman
(74) *Attorney, Agent, or Firm* — Pamela J. Sherwood; Bozicevic, Field & Francis LLP

(57) ABSTRACT

Methods are provided for targeting cells for depletion, including without limitation cancer cells, in a regimen comprising contacting the targeted cells with a combination of agents, including (i) an agent that blockades CD47 activity; and (ii) an antibody that specifically binds to EGFR. In some embodiments the cancer cells have a mutated form of one or more of KRAS, NRAS or BRAF. The level of depletion of the targeted cell is enhanced relative to a
(Continued)

regimen in which a single agent is used; and the effect may be synergistic relative to a regimen in which a single agent is used.

8 Claims, 5 Drawing Sheets

Specification includes a Sequence Listing.

Related U.S. Application Data

(60) Provisional application No. 62/380,177, filed on Aug. 26, 2016, provisional application No. 62/266,470, filed on Dec. 11, 2015.

(51) Int. Cl.
   *A61P 35/00* (2006.01)
   *A61K 39/00* (2006.01)

(52) U.S. Cl.
   CPC ...... *C07K 16/2803* (2013.01); *C07K 16/2839* (2013.01); *A61K 2039/507* (2013.01); *C07K 2317/76* (2013.01)

(56) References Cited

U.S. PATENT DOCUMENTS

| | | | |
|---|---|---|---|
| 9,944,911 B2 | 4/2018 | Ring et al. | |
| 10,081,680 B2 | 9/2018 | Weiskopf et al. | |
| 10,781,256 B2* | 9/2020 | Weiskopf | C07K 16/32 |
| 2014/0134158 A1 | 5/2014 | Baardelli et al. | |
| 2016/0333093 A1 | 11/2016 | Weiskopf et al. | |
| 2018/0251558 A1 | 9/2018 | Maute et al. | |

FOREIGN PATENT DOCUMENTS

| | | |
|---|---|---|
| WO | 2012/058592 A3 | 5/2012 |
| WO | 2014/087248 A2 | 6/2014 |
| WO | 2015/138600 A2 | 9/2015 |

OTHER PUBLICATIONS

Sorich et al., Extended RAS mutations and anti-EGFR monoclonal antibody survival benefit in metastatic colorectal cancer: a meta-analysis of randomized, controlled trials Annals Oncol. 26:13-21, Aug. 2014.*
Lutterbuese et al., T cell-engaging BiTE antibodies specific for EGFR potently eliminate KRAS- and BRAF-mutated colorectal cancer cells, Proc. Natl. Acad. Sci, 107(28):12605-12610, Jul. 2010.*
Poschau et al., EGFR and pi-integrin targeting differentially affect colorectal carcinoma cell radiosensitivity and invasion, Radiother. Oncol. 110(3): 510-516, Jun. 2015.*
Dalerba et al., "Phenotypic Characterization Of Human Colorectal Cancer Stem Cells" Proc Natl Acad Sci U S A, Jun. 12, 2007, pp. 10158-10163, 104(24), National Academy of Sciences, Washington, D.C.
Weiskopf et al., "Engineered Sirp alpha Variants As Immunotherapeutic Adjuvants To Anticancer Antibodies." Science, Jul. 5, 2013, pp. 88-91, 341(6141), American Association for the Advancement of Science, Washington, D.C.
Willingham et al. "The Cd47-Signal Regulatory Protein Alpha (Sirpa) Interaction Is A Therapeutic Target For Human Solid Tumors." Proc Natl Acad Sci U S A, Apr. 24, 2012, pp. 6662-6667, 109(17), National Academy of Sciences, Washington, D.C.
Ahmed et al., "Epigenetic and genetic features of 24 colon cancer cell lines", Oncogenesis, Jul. 29, 2013, pp. 1-8, Macmillan Publishers Limited, London, United Kingdom.
Chao et al., "Anti-Cd47 Antibody Synergizes With Rituximab To Promote Phagocytosis And Eradicate Non-Hodgkin Lymphoma", Cell, Sep. 3, 2010, pp. 699-713, 142(5), Elsevier Inc., Amsterdam, Netherlands.
Federal Drug Administration, ERBITUX prescribing information. [retrieved online Nov. 26, 2018] Retrieved from Internet: <https://www.accessdata.fda.gov/drugsatfda_docs/label/2012/125084502281bl.pdf>, revised Jan. 2012, pp. 1-31.
Blue Cross Blue Shield of North Carolina, Corporate medical policy, Retrieved from Internet: <https://www.bluecrossnc.com/sites/default/files/document/attachment/services/public/pdfs/medicalpolicy/kras_nras_braf_mutation_analysis_and_related_treatment_in_metastatic_colorectal_cancer.pdf> revised Aug. 2018., 6 Pages.
Steven et al., "Overcoming the challenges of topical antibody administration for improving healing outcomes: a review of recent laboratory and clinical approaches", Wound Practice & Research: Journal of the Australian Wound Management Association, Dec. 2017, pp. 188-194, vol. 25, Issue 4, Informit, Melbourne, Australia.
Matsukuma et al., "Rapid and simple detection of hot spot point mutations of epidermal growth factor receptor, BRAF, and N RAS in cancers using the loop-hybrid mobility shift assay", The Journal of Molecular Diagnostics, Sep. 2006, pp. 504-512, vol. 8, Issue 4, Elsevier, Amsterdam, Netherlands.
US Food and Drug Administration, Medical Guide: Epogen, Reference ID: 3138387, [Retreieved online May 7, 2018]. Retreived from: URL <www.fda.gov/downloads/Drugs/DrugSafety/ucm088591.pdf>. pp. 1-5, May 2012.
Weiskopf et al., "Engineered SIRP Variants as Immunotherapeutic Adjuvants to Anticancer Antibodies—Supp Materials", Science, Jul. 5, 2013, pp. 88-91, vol. 341, No. 6141, American Association for the Advancement of Science, Washington, DC.
Manna et al., "CD47 mediates killing of breast tumor cells via Gi-dependent inhibition of protein kinase A", Cancer Reserach, Feb. 1, 2004, pp. 1026-1036, vol. 64, No. 3, American Association for Cancer Research, Philadelphia, PA.
Liu et al. (2015) "Preclinical Development of a Humanized Anti-CD47 Antibody with Anti-Cancer Therapeutic Potential", PLoS One, e0137345, pp. 1-23).
Swiderek et al. (2013) "The interplay between epigenetic silencing, oncogenic KRas and HIF-1 regulatory pathways in control of BNIP3 expression in human colorectal cancer cells", Biochem. Biophys. Res. Commun , 441, [4], p. 707-712.

* cited by examiner

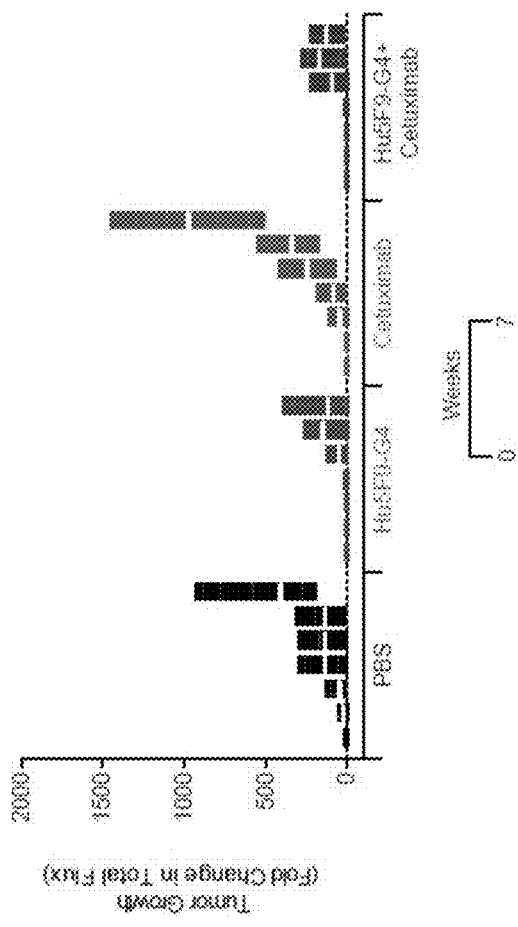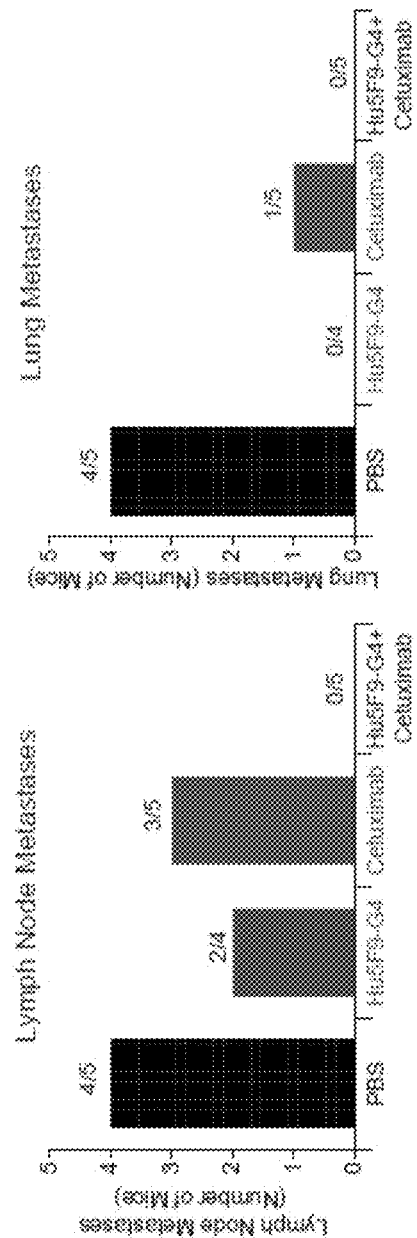
FIG. 4A
FIG. 4B
FIG. 4C

TREATMENT OF CANCER WITH DUAL TARGETING OF CD47 AND EGFR

CROSS REFERENCE

This application claims benefit and is a Continuation of application Ser. No. 15/373,150 filed Dec. 8, 2016, which claims benefit of U.S. Provisional Patent Application Nos. 62/380,177, filed Aug. 26, 2016, and 62/266,470, filed Dec. 11, 2015, which applications are incorporated herein by reference in their entirety.

FEDERALLY SPONSORED RESEARCH AND DEVELOPMENT

This invention was made with Government support under contract CA139490 awarded by the National Institutes of Health. The Government has certain rights in the invention.

INCORPORATION BY REFERENCE OF SEQUENCE LISTING PROVIDED AS A TEXT FILE

A sequence Listing is provided as a text file, (STAN-1288CON Sequence Listing.txt), created on (Feb. 9, 2021, and having a size of 1,382 bytes. The contents of the text file are incorporated by reference herein in their entirety.

Antibody-based therapy for cancer has become established as a successful and important strategy for treating patients with hematological malignancies and solid tumors. The definition of cell surface antigens that are expressed by human cancers has revealed a broad array of targets that are overexpressed, mutated or selectively expressed compared with normal tissues. A key challenge has been to identify antigens that are suitable for antibody-based therapeutics. Such therapeutics can function through mediating alterations in antigen or receptor function (such as agonist or antagonist functions), modulating the immune system or delivering a specific drug that is conjugated to an antibody that targets a specific antigen.

Depending on the antibody agent, killing of cancer cells can be the result of receptor blockade or agonist activity, induction of apoptosis, delivery of a drug or cytotoxic agent; immune-mediated cell killing mechanisms including, complement-dependent cytotoxicity (CDC), antibody-dependent cellular cytotoxicity (ADCC) and regulation of T cell function; and specific effects of an antibody on tumor vasculature and stroma. Antibodies that inhibit growth factors or growth factor receptors in cancer patients include CEA, epidermal growth factor receptor (EGFR; also known as ERBB1), ERBB2 (also known as HER2), ERBB3, MET (also known as HGFR), insulin-like growth factor 1 receptor (IGF1R), ephrin receptor A3 (EPHA3), tumor necrosis factor (TNF)-related apoptosis-inducing ligand receptor 1 (TRAILR1; also known as TNFRSF10A), TRAILR2 (also known as TNFRSF10B) and receptor activator of nuclear factor-κB ligand (RANKL; also known as TNFSF11).

Several anti-EGFR antibodies are currently in clinical use. Vectibix® (panitumumab) is an epidermal growth factor receptor antagonist approved as a single agent for the treatment of metastatic colorectal carcinoma with disease progression on or following chemotherapy regimens. Erbitux® (cetuximab) is an epidermal growth factor receptor (EGFR) antagonist approved for treatment of locally or regionally advanced squamous cell carcinoma of the head and neck; and as a single agent or combined with irinotecan for treatment of EGFR-expressing metastatic colorectal cancer. Nimotuzumab is a humanized IgG antibody against EGFR approved for use in some countries in Asia, South American and Africa for the treatment of head and neck cancer, glioma and nasopharyngeal cancer.

Antibodies that disrupt growth factor signaling, however, can be ineffective in the treatment of tumors where the signaling pathway is mutated. For example, many colorectal cancers carry mutations in the EGFR pathway that result in constitutive activation. Recent evidence has shown that patients with mutations in KRAS or NRAS do not respond to anti-EGFR antibodies, resulting in the approved use of these agents being restricted to patients with cancer in which KRAS is not mutated. The use of trastuzumab has also been restricted to patients with high levels of ERBB2 expression, as studies have shown that this is the group that derives maximum benefit from trastuzumab treatment.

Aside from targeting antigens that are involved in cancer cell proliferation and survival, antibodies can also function to either activate or antagonize immunological pathways that are important in cancer immune surveillance. It is now clear that an antigen-specific immune response is the result of a complex dynamic interplay between antigen-presenting cells, phagocytes, T lymphocytes and target cells.

For example, the cell surface protein CD47 on healthy cells and its engagement of a phagocyte receptor, SIRPα, constitutes a key "don't eat-me" signal that can turn off engulfment mediated by multiple modalities, including apoptotic cell clearance and FcR mediated phagocytosis. Blocking the CD47 mediated engagement of SIRPα on a phagocyte, or the loss of CD47 expression in knockout mice, can cause removal of live cells and non-aged erythrocytes. Alternatively, blocking SIRPα recognition also allows engulfment of targets that are not normally phagocytosed.

Related publications include U.S. Pat. No. 8,728,476; Dalerba, P., S. J. Dylla, Et Al. (2007). "Phenotypic Characterization Of Human Colorectal Cancer Stem Cells." Proc Natl Acad Sci USA 104(24): 10158-10163; Weiskopf, K., A. M. Ring, Et Al. (2013). "Engineered Sirp alpha Variants As Immunotherapeutic Adjuvants To Anticancer Antibodies." Science 341(6141): 88-91; Willingham, S. B., J. P. Volkmer, Et Al. (2012). "The Cd47-Signal Regulatory Protein Alpha (Sirpa) Interaction Is A Therapeutic Target For Human Solid Tumors." Proc Natl Acad Sci USA 109(17): 6662-6667. "Epigentic and genetic features of 24 colon cancer cell lines", Ahmed et al., Oncogenesis, 2013; Chao, M. P., A. A. Alizadeh, Et Al. (2010). "Anti-Cd47 Antibody Synergizes With Rituximab To Promote Phagocytosis And Eradicate Non-Hodgkin Lymphoma." Cell 142(5): 699-713.

SUMMARY OF THE INVENTION

Methods are provided for improved treatment of epidermal growth factor receptor (EGFR) expressing cancers in an individual, which cancers include without limitation any EGFR-expressing cancer, e.g. carcinomas such as adenocarcinomas, squamous cell carcinomas, basal cell carcinomas, renal cell carcinomas; and gliomas. Cancers of interest may include colorectal carcinomas, non-small cell lung carcinoma (NSCLC), ovarian cancer, pancreatic cancer, breast cancer, squamous cell carcinomas, and gliomas. In the methods of the invention, cancer cells are contacted with a combination of (a) an agent that blocks signaling between CD47 and SIRPα; and (b) an antibody that specifically binds to EGFR. The methods of the invention can provide for increased overall survival of the individual being treated, in contrast to treatment with known EGFR antagonist antibodies in the absence of CD47 blockade.

In some embodiments the EGFR-expressing cancer cells comprise a mutation that results in constitutive activation of the EGFR signaling pathway. In some such embodiments the mutation is a KRAS, NRAS or BRAF mutation in one or both alleles. In some embodiments the mutation is in codon 12 or 13 of KRAS. Such individuals are excluded from therapy with anti-EGFR antagonist antibodies, but are shown herein to benefit from treatment with the combination therapy of the present invention. In other embodiments individuals having wild-type KRAS, NRAS, BRAF are treated by the methods of the invention.

Individuals may be selected for therapy by determining the genotype of the cancer cells with respect to one or more of KRAS, NRAS and BRAF. Individuals currently excluded from therapy with anti-EGFR antibodies due to the presence of a mutation in KRAS or NRAS can be selected for treatment with the methods of the present invention. Individuals may also be tested for the expression of detectable EGFR on the cancer cells, where cancers showing positive expression of EGFR are selected for treatment.

The agents in the combination are administered concomitantly, i.e. each agent is administered within about 45 days, 30 days, 15 days, 7 days, 3 days, 2 days, 1 day or substantially simultaneously with respect to the other agent(s) in the combination. The agents can be considered to be combined if administration scheduling is such that the serum level of both agents is at a therapeutic level. A benefit of the present invention can be the use of lowered doses of the anti-EGFR antibody relative to the dose required as a monotherapy. Administration may be repeated as necessary for depletion of the cancer cell population.

In some embodiments a primer agent is administered prior to administering a therapeutically effective dose of an anti-CD47 agent to the individual. Suitable primer agents include an erythropoiesis-stimulating agent (ESA), and/or a priming dose of an anti-CD47 agent. Following administration of the priming agent, and allowing a period of time effective for an increase in reticulocyte production, a therapeutic dose of an anti-CD47 agent is administered. The therapeutic dose can be administered in number of different ways. In some embodiments, two or more therapeutically effective doses are administered after a primer agent is administered. In some embodiments a therapeutically effective dose of an anti-CD47 agent is administered as two or more doses of escalating concentration, in others the doses are equivalent.

In some embodiments, administration of a combination of agents of the invention is combined with an effective dose of an agent that increases patient hematocrit, for example erythropoietin stimulating agents (ESA). Such agents are known and used in the art, including, for example, Aranesp® (darbepoetin alfa), Epogen®NF/Procrit®NF (epoetin alfa), Omontys® (peginesatide), Procrit®, etc.

An anti-CD47 agent for use in the methods of the invention interferes with binding between CD47 present on the cancer cell and SIRPα present on a phagocytic cell. Such methods, in the presence of the anti-EGFR antibody, can increase phagocytosis of the cancer cell. Suitable anti-CD47 agents include soluble SIRPα polypeptides; soluble CD47; anti-CD47 antibodies, anti-SIRPα antibodies, and the like, where the term antibodies encompasses antibody fragments and variants thereof, as known in the art. In some embodiments the anti-CD47 agent is an anti-CD47 antibody. In some embodiments the anti-CD47 antibody is a non-hemolytic antibody. In some embodiments the antibody comprises a human IgG4 Fc region.

Anti-EGFR antibodies include, without limitation, antibodies in current clinical use and in clinical trials, which include antibodies that act through antagonizing EGFR signaling. While such EGFR antagonist antibodies can be used for the methods of the invention, the methods of the invention do not require that the anti-EGFR antibody block EGFR signaling, and thus antibodies that are not pathway antagonists can be used in the present combination therapy methods. Examples of anti-EGFR antibodies currently approved for clinical use include the chimeric monoclonal antibody cetuximab; which contains the murine variable region of mAb225 and a human IgG1 constant region; the fully human IgG2 antibody panitumumab; and the humanized IgG1 antibody nimotuzumab. Other antibodies in clinical development include zalutumumab and matuzumab. The anti-EGFR antibody may be administered in accordance with conventional dosing suitable as a monotherapy or combined with chemotherapy and/or radiation; or the dosage may be adjusted to optimize the effectiveness when combined with CD47 blockade.

The contacting of a cancer cells may be performed in vivo, e.g. for therapeutic purposes, and in vitro, e.g. for screening assays and the like. Tumor cells, e.g. carcinomas, gliomas, melanomas, etc. are targeted for depletion by contacting the immune cells, including phagocytic cells, in proximity of the tumor cells with a combination of a CD47 blocking agent that is effective to block the interaction between CD47 and SIRPα, and an anti-EGFR antibody. The combination therapy can be synergistic in enhancing phagocytosis and elimination of tumor cells as compared to the use of single agents. The combination may also induce an anti-tumor T cell response. Further, the combination can provide for increased overall survival of the individual that is treated.

BRIEF DESCRIPTION OF THE FIGURES

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

G4) enhances therapeutic efficacy in vivo. (FIG. 3A). Tumor Growth. UM8 colon adenocarcinoma cells (EGFR⁺) transduced with GFP-luciferase encoding lentivirus were subcutaneously injected into the backs of NSG mice. Twenty-eight days after tumor cell engraftment (confirmed by bioluminescence imaging), PBS (black), Hu5F9-G4 (red) (250 µg), cetuximab (green 120 µg), panitumumab (blue) (120 µg), Hu5F9-G4 in combination with cetuximab (orange), or Hu5F9-G4 in combination with panitumumab (purple) were administered via IP injection every other day (PBS, Hu5F9-G4) or weekly (panitumumab, cetuximab) for thirteen weeks. Tumor growth was measured by bioluminescence imaging. Administration of Hu5F9-G4 alone did not inhibit tumor growth, and treatment with cetuximab monotherapy stabilized tumor growth but failed to produce a tumor regression. Treatment with panitumumab monotherapy induced a minor tumor regression while a major tumor regression was observed in all mice treated with Hu5F9-G4 in combination with cetuximab or panitumumab. (FIG. 3B). Survival Curve.

FIG. 4A-4C. Combination of anti-EGFR antibodies (cetuximab) with blockade of the CD47-SIRPα signaling pathway by anti-CD47 antibody (Hu5F9-G4) enhances antibody dependent cellular phagocytosis (ADCP) of EGFR-expressing cancer cells irrespective of downstream mutations in the EGFR signaling pathway and prevents or eliminates metastasis. (FIG. 4A). DLD1 colon adenocarcinoma cells (EGFR⁺, KRAS mutant) transduced with GFP-lucif erase encoding lentivirus were subcutaneously injected into the backs of NSG mice. Five days after tumor cell engraftment (confirmed by bioluminescence imaging), PBS (black), Hu5F9-G4 (red) (250 µg), cetuximab (green) (120 µg), or Hu5F9-G4 in combination with cetuximab (blue) were administered via IP injection every other day (PBS, Hu5F9-G4) or weekly (cetuximab) for seven weeks. Tumor growth was measured by bioluminescence imaging. Administration of Hu5F9-G4 alone slowed but did not inhibit tumor growth. Treatment with cetuximab monotherapy had no effect as expected for tumors with downstream mutations in the EGFR signaling pathway. Hu5F9-G4 in combination with cetuximab did not inhibit tumor growth but had the strongest effect to slow down tumor growth. (FIG. 4B and FIG. 4C). Remarkably, mice treated with cetuximab had less lymph node (4/5 mice) and lung metastasis (1/5 mice) compared to PBS control cohort (LN 4/5 and lung 4/5) but the therapeutic effect was less potent than with Hu5F9-G4 (LN 2/4 and lung 0/4). The strongest therapeutic effect had the combination Hu5F9-G4 with cetuximab. None of the mice in this cohort had any metastasis at the end of treatment (LN 0/5 and lung 0/5).

DETAILED DESCRIPTION OF THE EMBODIMENTS

Figure 1:
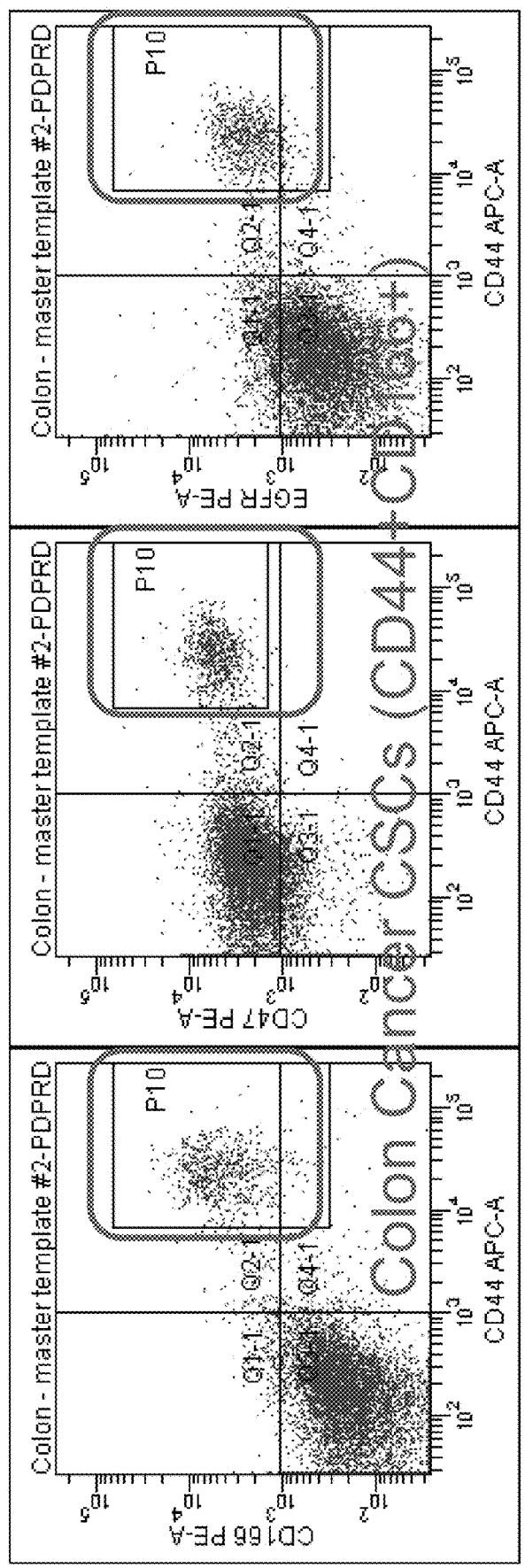
FIG. 1. Expression of EGFR on cancer stem cells. Patient colon cancer cells were profiled for markers indicative of cancer stem cells (CD44+ CD166+) as well as expression of CD47 and EGFR. It is shown that most if not all CSCs co-express EGFR.
Figure 2:
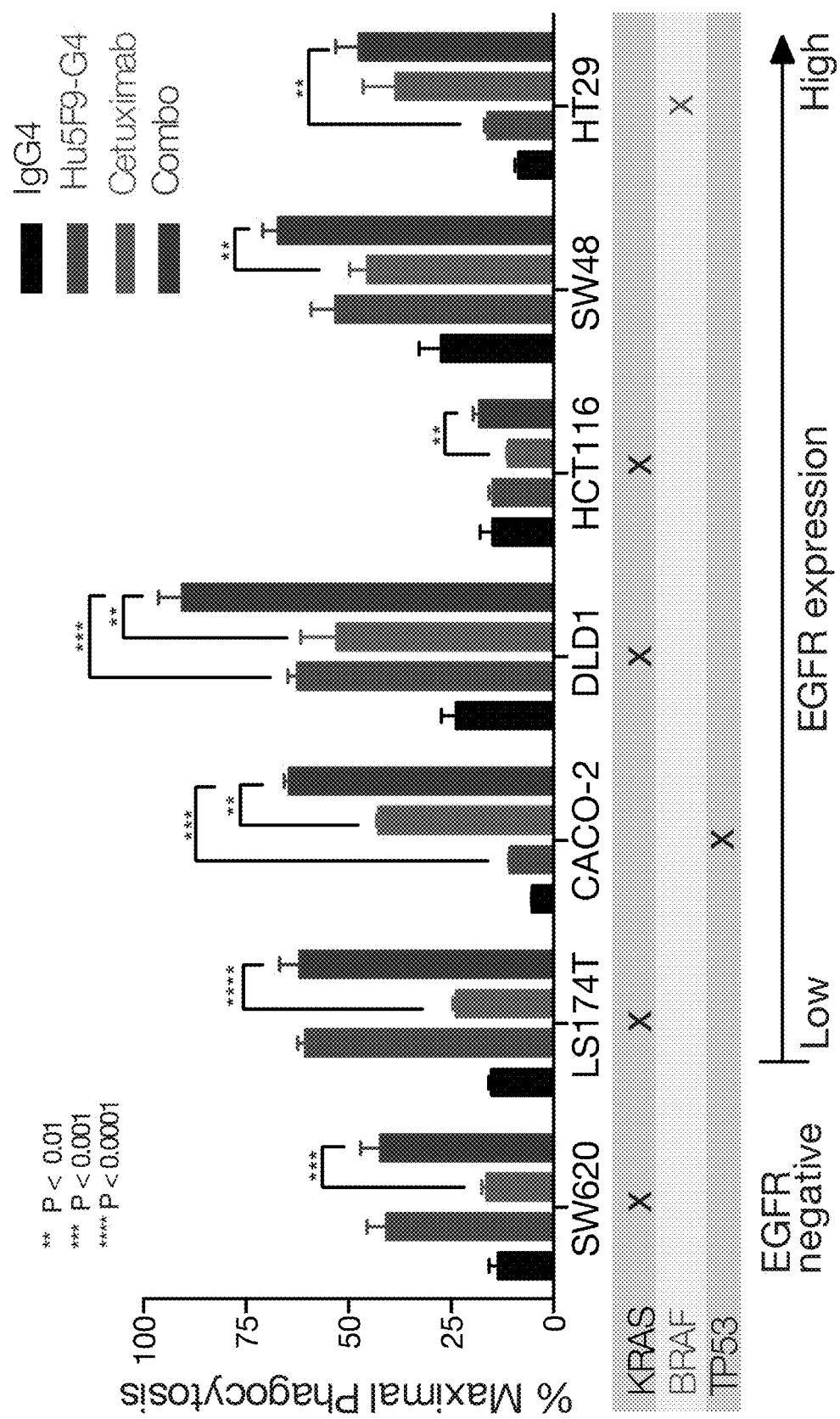
FIG. 2. Blockade of the CD47-SIRPα pathway (anti-CD47 Ab, Hu5F9-G4) enhances antibody dependent cellular phagocytosis (ADCP) of EGFR-expressing cancer cells by anti-EGFR antibodies (cetuximab) irrespective of downstream mutations in the EGFR signaling pathway. Phagocytosis of a panel of colon cancer cells by donor-derived human macrophages in the presence of control IgG4 (black), anti-CD47 Ab Hu5F9-G4 (red), anti-EGFR Ab cetuximab (green), or combination of Hu5F9-G4 with cetuximab (blue). Mutational status of KRAS and BRAF as previously reported (*Epigentic and genetic features of 24 colon cancer cell lines*, Ahmed et al., *Oncogenesis*, 2013). Cells are organized by increasing expression of EGFR; SW620 is negative for EGFR expression as determined by cetuximab binding by flow cytometry. Data represent mean and standard deviation using macrophages from 2 independent blood donors.
Figure 3A:
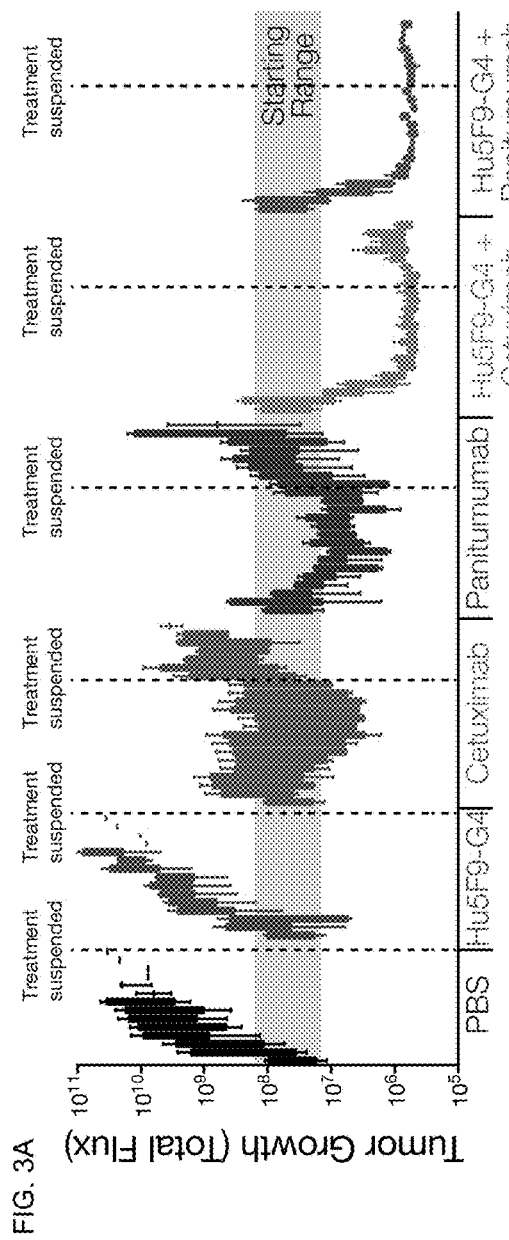
FIG. 3A-FIG. 3B. Combination of anti-EGFR antibodies (cetuximab, panitumumab) with blockade of the CD47-SIRPα signaling pathway by anti-CD47 antibody (Hu5F9-
Figure 3B:
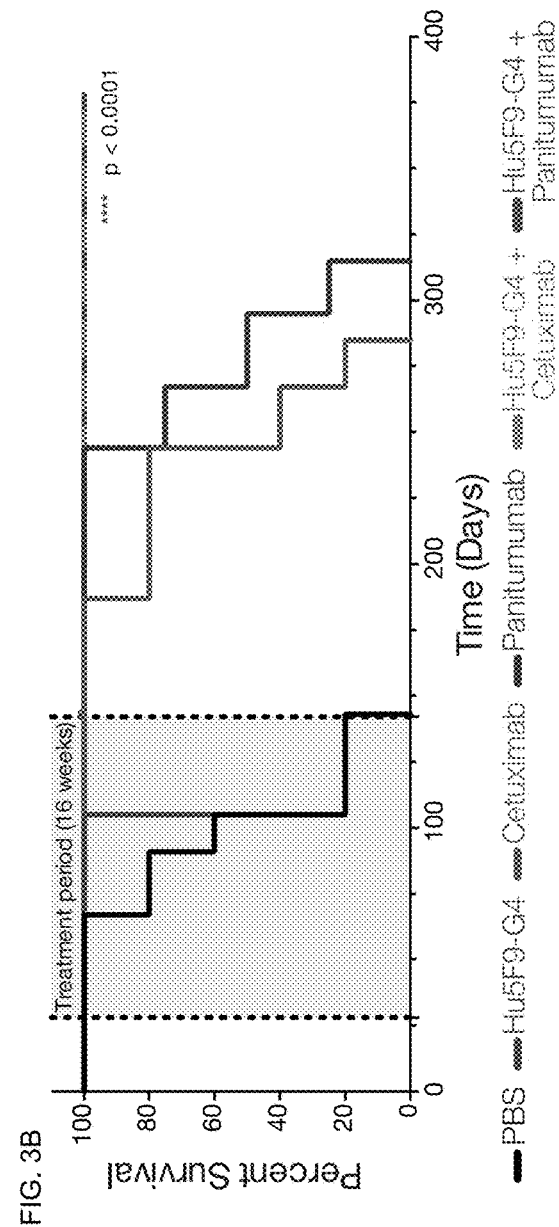
Figure 5:
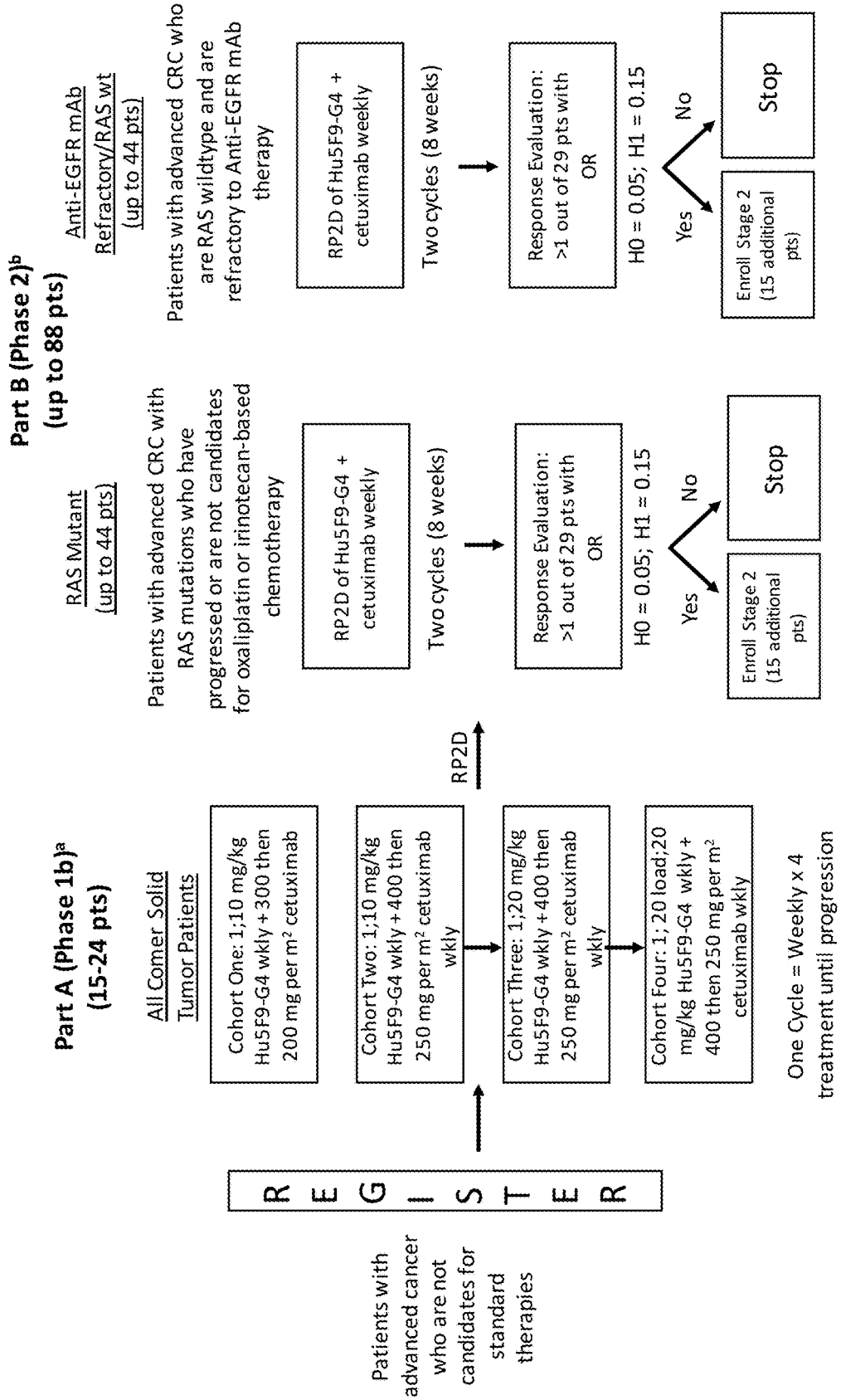
FIG. 5. Schematic of clinical trial protocol, showing dosing and timing of combination.

Methods are provided for the targeted depletion of EGFR-expressing cancer cells in a subject, where the cancer cells are selectively ablated by phagocytosis of the living cells, following contacting with a combination of agents that (a) block CD47 signaling; and (b) target EGFR.

To facilitate an understanding of the invention, a number of terms are defined below.

Before the present active agents and methods are described, it is to be understood that this invention is not limited to the particular methodology, products, apparatus and factors described, as such methods, apparatus and formulations may, of course, vary. It is also to be understood that the terminology used herein is for the purpose of describing particular embodiments only, and is not intended to limit the scope of the present invention which will be limited only by appended claims.

It must be noted that as used herein and in the appended claims, the singular forms "a," "and," and "the" include plural referents unless the context clearly dictates otherwise. Thus, for example, reference to "a drug candidate" refers to one or mixtures of such candidates, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Generally, conventional methods of protein synthesis, recombinant cell culture and protein isolation, and recombinant DNA techniques within the skill of the art are employed in the present invention. Such techniques are explained fully in the literature, see, e.g., Maniatis, Fritsch & Sambrook, Molecular Cloning: A Laboratory Manual (1982); Sambrook, Russell and Sambrook, Molecular Cloning: A Laboratory Manual (2001); Harlow, Lane and Harlow, Using Antibodies: A Laboratory Manual: Portable Protocol No. I, Cold Spring Harbor Laboratory (1998); and Harlow and Lane, Antibodies: A Laboratory Manual, Cold Spring Harbor Laboratory; (1988).

Definitions

Anti-CD47 Agent.

CD47 is a broadly expressed transmembrane glycoprotein with a single Ig-like domain and five membrane spanning regions, which functions as a cellular ligand for SIRPα with binding mediated through the NH2-terminal V-like domain of SIRPα. SIRPα is expressed primarily on myeloid cells, including macrophages, granulocytes, myeloid dendritic cells (DCs), mast cells, and their precursors, including hematopoietic stem cells. Structural determinants on SIRPα that mediate CD47 binding are discussed by Lee et al. (2007) J. Immunol. 179:7741-7750; Hatherley et al. (2008) Mol Cell. 31(2):266-77; Hatherley et al. (2007) J. B. C.

282:14567-75; and the role of SIRPα cis dimerization in CD47 binding is discussed by Lee et al. (2010) J. B. C. 285:37953-63. In keeping with the role of CD47 to inhibit phagocytosis of normal cells, there is evidence that it is transiently upregulated on hematopoietic stem cells (HSCs) and progenitors just prior to and during their migratory phase, and that the level of CD47 on these cells determines the probability that they are engulfed in vivo.

As used herein, the term "anti-CD47 agent" or "agent that provides for CD47 blockade" refers to any agent that reduces the binding of CD47 (e.g., on a target cell) to SIRPα (e.g., on a phagocytic cell). Non-limiting examples of suitable anti-CD47 reagents include SIRPα reagents, including without limitation high affinity SIRPα polypeptides, anti-SIRPα antibodies, soluble CD47 polypeptides, and anti-CD47 antibodies or antibody fragments. In some embodiments, a suitable anti-CD47 agent (e.g. an anti-CD47 antibody, a SIRPα reagent, etc.) specifically binds CD47 to reduce the binding of CD47 to SIRPα.

In some embodiments, a suitable anti-CD47 agent (e.g., an anti-SIRPα antibody, a soluble CD47 polypeptide, etc.) specifically binds SIRPα to reduce the binding of CD47 to SIRPα. A suitable anti-CD47 agent that binds SIRPα does not activate SIRPα (e.g., in the SIRPα-expressing phagocytic cell). The efficacy of a suitable anti-CD47 agent can be assessed by assaying the agent. In an exemplary assay, target cells are incubated in the presence or absence of the candidate agent and in the presence of an effector cell, e.g. a macrophage or other phagocytic cell. An agent for use in the methods of the invention will up-regulate phagocytosis by at least 5% (e.g., at least 10%, at least 20%, at least 30%, at least 40%, at least 50%, at least 60%, at least 70%, at least 80%, at least 90%, at least 100%, at least 120%, at least 140%, at least 160%, at least 180%, at least 200%, at least 500%, at least 1000%) compared to phagocytosis in the absence of the agent. Similarly, an in vitro assay for levels of tyrosine phosphorylation of SIRPα will show a decrease in phosphorylation by at least 5% (e.g., at least 10%, at least 15%, at least 20%, at least 30%, at least 40%, at least 50%, at least 60%, at least 70%, at least 80%, at least 90%, or 100%) compared to phosphorylation observed in absence of the candidate agent.

In some embodiments, the anti-CD47 agent does not activate CD47 upon binding. When CD47 is activated, a process akin to apoptosis (i.e., programmed cell death) may occur (Manna and Frazier, Cancer Research, 64, 1026-1036, Feb. 1 2004). Thus, in some embodiments, the anti-CD47 agent does not directly induce cell death of a CD47-expressing cell.

In some embodiments a primer agent is administered prior to administering a therapeutically effective dose of an anti-CD47 agent to the individual. Suitable primer agents include an erythropoiesis-stimulating agent (ESA), and/or a priming dose of an anti-CD47 agent. Following administration of the priming agent, and allowing a period of time effective for an increase in reticulocyte production, a therapeutic dose of an anti-CD47 agent is administered. Administration may be made in accordance with the methods described in co-pending patent application U.S. Ser. No. 14/769,069, herein specifically incorporated by reference.

SIRPα Reagent.

A SIRPα reagent comprises the portion of SIRPα that is sufficient to bind CD47 at a recognizable affinity, which normally lies between the signal sequence and the transmembrane domain, or a fragment thereof that retains the binding activity. A suitable SIRPα reagent reduces (e.g., blocks, prevents, etc.) the interaction between the native proteins SIRPα and CD47. The SIRPα reagent will usually comprise at least the d1 domain of SIRPα.

In some embodiments, a subject anti-CD47 agent is a "high affinity SIRPα reagent", which includes SIRPα-derived polypeptides and analogs thereof (e.g., CV1-hIgG4, and CV1 monomer). High affinity SIRPα reagents are described in international application PCT/US13/21937, which is hereby specifically incorporated by reference. High affinity SIRPα reagents are variants of the native SIRPα protein. The amino acid changes that provide for increased affinity are localized in the d1 domain, and thus high affinity SIRPα reagents comprise a d1 domain of human SIRPα, with at least one amino acid change relative to the wild-type sequence within the d1 domain. Such a high affinity SIRPα reagent optionally comprises additional amino acid sequences, for example antibody Fc sequences; portions of the wild-type human SIRPα protein other than the d1 domain, including without limitation residues 150 to 374 of the native protein or fragments thereof, usually fragments contiguous with the d1 domain; and the like. High affinity SIRPα reagents may be monomeric or multimeric, i.e. dimer, trimer, tetramer, etc. In some embodiments, a high affinity SIRPα reagent is soluble, where the polypeptide lacks the SIRPα transmembrane domain and comprises at least one amino acid change relative to the wild-type SIRPα sequence, and wherein the amino acid change increases the affinity of the SIRPα polypeptide binding to CD47, for example by decreasing the off-rate by at least 10-fold, at least 20-fold, at least 50-fold, at least 100-fold, at least 500-fold, or more.

Optionally the SIRPα reagent is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules.

Anti-CD47 Antibodies.

In some embodiments, a subject anti-CD47 agent is an antibody that specifically binds CD47 (i.e., an anti-CD47 antibody) and reduces the interaction between CD47 on one cell (e.g., an infected cell) and SIRPα on another cell (e.g., a phagocytic cell). In some embodiments, a suitable anti-CD47 antibody does not activate CD47 upon binding. Some anti-CD47 antibodies do not reduce the binding of CD47 to SIRPα (and are therefore not considered to be an "anti-CD47 agent" herein) and such an antibody can be referred to as a "non-blocking anti-CD47 antibody." A suitable anti-CD47 antibody that is an "anti-CD47 agent" can be referred to as a "CD47-blocking antibody". Non-limiting examples of suitable antibodies include clones B6H12, 5F9, 8B6, and C3 (for example as described in International Patent Publication WO 2011/143624, herein specifically incorporated by reference). The 5F9 antibody comprises CDR sequences (SEQ ID NO:1) 5F9 heavy chain CDR1: NYNMH; (SEQ ID NO:2) 5F9 heavy chain CDR2: TIYPGNDDTSYNQKFKD; (SEQ ID NO:3) 5F9 heavy chain CDR3: GGYRAMDY; (SEQ ID NO:4) 5F9 light chain CDR1: RSSQSIVYSNGNTYLG; (SEQ ID NO:5) 5F9 light chain CDR2: KVSNRFS; (SEQ ID NO:6) 5F9 light chain CDR3: FQGSHVPYT. Suitable anti-CD47 antibodies include fully human, humanized or chimeric versions of such antibodies. Humanized antibodies (e.g., hu5F9-G4) are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

In some embodiments an anti-CD47 antibody comprises a human IgG Fc region, e.g. an IgG1, IgG2a, IgG2b, IgG3, IgG4 constant region. In a preferred embodiment the IgG Fc region is an IgG4 constant region. The IgG4 hinge may be stabilized by the amino acid substitution S241P (see Angal et al. (1993) Mol. Immunol. 30(1):105-108, herein specifically incorporated by reference).

Anti-SIRPα Antibodies.

In some embodiments, a subject anti-CD47 agent is an antibody that specifically binds SIRPα (i.e., an anti-SIRPα antibody) and reduces the interaction between CD47 on one cell (e.g., an infected cell) and SIRPα on another cell (e.g., a phagocytic cell). Suitable anti-SIRPα antibodies can bind SIRPα without activating or stimulating signaling through SIRPα because activation of SIRPα would inhibit phagocytosis. Instead, suitable anti-SIRPα antibodies facilitate the preferential phagocytosis of inflicted cells over normal cells. Those cells that express higher levels of CD47 (e.g., infected cells) relative to other cells (non-infected cells) will be preferentially phagocytosed. Thus, a suitable anti-SIRPα antibody specifically binds SIRPα (without activating/stimulating enough of a signaling response to inhibit phagocytosis) and blocks an interaction between SIRPα and CD47. Suitable anti-SIRPα antibodies include fully human, humanized or chimeric versions of such antibodies. Humanized antibodies are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Soluble CD47 Polypeptides.

In some embodiments, a subject anti-CD47 agent is a soluble CD47 polypeptide that specifically binds SIRPα and reduces the interaction between CD47 on one cell (e.g., an infected cell) and SIRPα on another cell (e.g., a phagocytic cell). A suitable soluble CD47 polypeptide can bind SIRPα without activating or stimulating signaling through SIRPα because activation of SIRPα would inhibit phagocytosis. Instead, suitable soluble CD47 polypeptides facilitate the preferential phagocytosis of infected cells over non-infected cells. Those cells that express higher levels of CD47 (e.g., infected cells) relative to normal, non-target cells (normal cells) will be preferentially phagocytosed. Thus, a suitable soluble CD47 polypeptide specifically binds SIRPα without activating/stimulating enough of a signaling response to inhibit phagocytosis.

In some cases, a suitable soluble CD47 polypeptide can be a fusion protein (for example as structurally described in US Patent Publication US20100239579, herein specifically incorporated by reference). However, only fusion proteins that do not activate/stimulate SIRPα are suitable for the methods provided herein. Suitable soluble CD47 polypeptides also include any peptide or peptide fragment comprising variant or naturally existing CD47 sequences (e.g., extracellular domain sequences or extracellular domain variants) that can specifically bind SIRPα and inhibit the interaction between CD47 and SIRPα without stimulating enough SIRPα activity to inhibit phagocytosis.

In certain embodiments, soluble CD47 polypeptide comprises the extracellular domain of CD47, including the signal peptide, such that the extracellular portion of CD47 is typically 142 amino acids in length. The soluble CD47 polypeptides described herein also include CD47 extracellular domain variants that comprise an amino acid sequence at least 65%-75%, 75%-80%, 80-85%, 85%-90%, or 95%-99% (or any percent identity not specifically enumerated between 65% to 100%), which variants retain the capability to bind to SIRPα without stimulating SIRPα signaling.

In certain embodiments, the signal peptide amino acid sequence may be substituted with a signal peptide amino acid sequence that is derived from another polypeptide (e.g., for example, an immunoglobulin or CTLA4). For example, unlike full-length CD47, which is a cell surface polypeptide that traverses the outer cell membrane, the soluble CD47 polypeptides are secreted; accordingly, a polynucleotide encoding a soluble CD47 polypeptide may include a nucleotide sequence encoding a signal peptide that is associated with a polypeptide that is normally secreted from a cell.

In other embodiments, the soluble CD47 polypeptide comprises an extracellular domain of CD47 that lacks the signal peptide. As described herein, signal peptides are not exposed on the cell surface of a secreted or transmembrane protein because either the signal peptide is cleaved during translocation of the protein or the signal peptide remains anchored in the outer cell membrane (such a peptide is also called a signal anchor). The signal peptide sequence of CD47 is believed to be cleaved from the precursor CD47 polypeptide in vivo.

In other embodiments, a soluble CD47 polypeptide comprises a CD47 extracellular domain variant. Such a soluble CD47 polypeptide retains the capability to bind to SIRPα without stimulating SIRPα signaling. The CD47 extracellular domain variant may have an amino acid sequence that is at least 65%-75%, 75%-80%, 80-85%, 85%-90%, or 95%-99% identical (which includes any percent identity between any one of the described ranges) to the native CD47 sequence.

EGFR.

Epidermal growth factor receptor (EGFR) exists on the cell surface and is activated by binding of its specific ligands, including epidermal growth factor and transforming growth factor α (TGFα). Upon activation by its growth factor ligands, EGFR undergoes a transition from an inactive monomeric form to an active dimer. EGFR dimerization stimulates its intrinsic intracellular protein-tyrosine kinase activity. As a result, autophosphorylation of several tyrosine (Y) residues in the C-terminal domain of EGFR occurs. This autophosphorylation elicits downstream activation and signaling by several other proteins that associate with the phosphorylated tyrosines through their own phosphotyrosine-binding SH2 domains. These downstream signaling proteins initiate several signal transduction cascades, principally the MAPK, Akt and JNK pathways, leading to DNA synthesis and cell proliferation.

Downstream effects of EGFR activation include modulation of three major pathways. Induction of the RAS-RAF-MAPK pathway occurs when phosphorylated EGFR recruits the guanine-nucleotide exchange factor via the GRB2 and SHC adapter proteins, which activates RAS. This step subsequently stimulates RAF and the MAP kinase pathway, ultimately affecting cell proliferation, tumor invasion, and metastasis. The involvement of RAS in the EGFR signaling pathway is of importance for treatment with anti-EGFR antagonist antibodies. EGFR inhibitors are effective in only a small subset of patients, despite high levels of EGFR expression. Some cancers appear to acquire resistance to EGFR inhibitors, and multiple mechanisms seem to underlie the lack of sensitivity to the targeted therapies, including mutations in the EGFR gene itself, as well as in downstream effectors such as RAS, RAF, and AKT that are associated with differential clinical outcomes.

The EGFR gene is present on chromosome 7p11.2 and has 28 exons coding for a transmembrane receptor protein of 464 amino acids. Within EGFR, exons 5-7 and 13-16 code for the ligand binding domain while exons 18-24 code for the TK domain. Autophosphorylation occurs in the region encoded by exons 25-28.

Mutations, amplifications or misregulations of EGFR or family members are implicated in about 30% of all epithelial cancers. Although mutations can occur anywhere within the TK domain, a significant set of EGFR mutations in lung cancer are observed in exons 18-21. The most frequent of these are in-frame deletions in exon 19 that occur in approximately 45% of cases, followed by point mutations in exon 21, in 40-45% of cases. While more than 20 different deletions are observed in exon 19, L858R in exon 21 is the most common point mutation detected. De novo mutations are known to occur within EGFR that constitutively turn on the receptor. While the most important of these is T790M, a point mutation in exon 20 that accounts for about 50% of cases, insertional mutations in exon 20, which occur in about 5% of cases, have also been associated with resistance.

Mutations in KRAS at codons 12 and 13 occur in about 15-50% of NSCLC patients, while BRAF mutations are detected in 1-2% of lung cancer patients. KRAS and EGFR mutations appear to be mutually exclusive in NSCLC, with EGFR mutations occurring in non-smokers and KRAS mutations in smokers. Approximately 30% to 50% of colorectal tumors are known to have a mutated KRAS gene. A mutated BRAFgene, which is present in 5% to 10% of tumors, may also affect response to anti-EGFR antibodies.

KRAS, NRAS, BRAF Mutations.

Multiple studies have shown that patients with tumors harboring mutations in KRAS or NRAS exons 2, 3, or 4 predict lack of response to anti-EGFR antibody therapy given in combination with chemotherapy (Ciardiello et al. 2014; Douillard et al. 2013; Karthaus et al. 2013; Peeters et al. 2014; Stintzing et al. 2014; Tejpar et al. 2014). Specific mutations of interest include KRAS mutations in codon 12 or 13, for including without limitation KRAS c.34G>T (G12C); KRAS c.34G>C (G12R); KRAS c.34G>A (G12S); KRAS c.35G>C (G12A); KRAS c.35G>A (G12D); KRAS c.35G>T (G12V); KRAS c.37G>T (G13C); KRAS c.37G>C (G13R); KRAS c.37G>A (G13S); KRAS c.38G>C (G13A); KRAS c.38G>A (G13D); NRAS c.34G>T (G12C); NRAS c.34G>A (G12S); NRAS c.35G>C (G12A); NRAS c.35G>A (G12D); NRAS c.35G>T (G12V). The four most frequent KRAS mutations, G12D, G12V, G13D, G12C, account for 83% of all KRAS mutations. See, for example, Peeters et al. JCO Feb. 20, 2013 vol. 31 no. 6 759-765; Stoltze et al. Scientific Reports 5, Article number: 8535 (2015).

Various methods known in the art can be used for analysis of the genotype of these genes. Traditional methods for detecting mutations involved screening by direct DNA sequencing of the tumor tissue. Sanger sequencing technology is available in most molecular diagnostic laboratories, and it has the singular advantage of detecting alterations across a gene, including novel variants. Recent methodologies have focused on targeted screening of mutations to achieve more rapid, robust, and sensitive tests. Molecular diagnostic laboratories currently use a variety of methods, including amplification refractory mutation system, pyrosequencing, smart amplification process, high-resolution melting analysis, and restriction fragment length polymorphism, to name a few. These methods all distinguish between mutant and wild-type DNA within the region of interest. In contrast to direct sequencing, the limit of detection for targeted analysis is ~1-5% mutant DNA in the background of normal DNA.

Most laboratories use formalin-fixed, paraffin-embedded (FFPE) tissue to test for mutations. A few also use frozen tumor tissue. However, screening FFPE samples poses significant challenges, including successfully extracting the DNA, interferences from the fixatives used for embedding tissue, and most importantly, obtaining shorter amplicons for effective analysis, particularly if a PCR-based methodology is used. Alternate sample types such as fine needle aspirates and pleural effusions are currently being evaluated as viable options to enable quicker, easier diagnosis of malignancy. Micro-dissection of the tumor prior to testing is also helpful as it effectively enriches the sample, thereby increasing sensitivity.

A commercially available test for this purpose is therascreen KRAS RGQ (Rotor-Gene Q) PCR (polymerase chain reaction) Kit. Tests for mutations in codons 12 or 13 of the KRAS gene can be performed on formalin-fixed, paraffin-embedded tissue from the primary tumor or a metastasis. PCR amplification and DNA sequence analysis or allele-specific PCR for BRAF V600E mutation status on formalin-fixed, paraffin-embedded tissue from the primary tumor or a metastasis Anti-EGFR Antibody.

A number of clinically useful antibodies that specifically bind to and inhibit human EGFR are available and find use in the methods of the invention. Anti-EGFR monoclonal antibodies, for example cetuximab, panitumumab, nimotuzumab, zalutumumab, and matuzumab bind to the extracellular domain of the EGFR monomer and compete for receptor binding by the endogenous ligands, triggering receptor internalization and blocking ligand-induced receptor activation. Cetuximab, which binds to the L2 domain of EGFR, is a chimeric protein antibody composed of variable and constant regions from mouse and human sources, respectively, while panitumumab and nimotuzumab are human and humanized antibodies. To date, the Food and Drug Administration has approved EGFR-targeted mAbs for use in advanced colorectal cancer, gliomas, and head and neck tumors.

The antibodies may be used as currently prescribed, or the dosage may be varied to optimize the combination therapy. For example, cetuximab is currently prescribed at a dose of 400 mg/m$^2$ as an initial dose followed by 250 mg/m$^2$ weekly infusion. The dose may be reduced by 50% for non-serious infusion reactions. Panitumumab is currently prescribed at 6 mg/kg every 14 days as an intravenous infusion. The dose may be reduced by 50% for non-serious infusion reactions.

For example, anti-EGFR antibodies may be administered at a dose of from about 0.05 mg/kg, 0.1 mg/kg; 0.5 mg/kg, 1 mg/kg, 2.5 mg/kg, 5 mg/kg, 7.5 mg/kg, 10 mg/kg, 12.5 mg/kg, 15 mg/kg, or more as required. Dosing may be daily, every other day, semi-weekly, weekly, every 145 days, etc. for a period of time sufficient to achieve the desired result, e.g. from about 1, 2, 3, 4, 5, 6, 7, 8, 9, 10, 11, 12 or more weeks. In some embodiments the dose for a combination therapy is lower than the dose required for effectiveness as a monotherapy.

In addition to antibodies that directly inhibit EGFR signaling, the combination methods of the present invention find use with non-antagonistic antibodies, e.g. as described in international patent application WO2012058592 (herein specifically incorporated by reference); the non-antagonistic anti-EGFR antibody 13A9; and the like.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies. The term "antibody" also includes antigen binding forms of antibodies, including fragments with antigen-binding capability (e.g., Fab', F(ab')$_2$, Fab, Fv and rIgG. The term also refers to recombinant single chain Fv fragments (scFv). The term antibody also includes bivalent or bispecific molecules, diabodies, triabodies, and tetrabodies.

Selection of antibodies may be based on a variety of criteria, including selectivity, affinity, cytotoxicity, etc. The phrase "specifically (or selectively) binds" to an antibody or "specifically (or selectively) immunoreactive with," when referring to a protein or peptide, refers to a binding reaction that is determinative of the presence of the protein, in a heterogeneous population of proteins and other biologics. Thus, under designated immunoassay conditions, the specified antibodies bind to a particular protein sequences at least two times the background and more typically more than 10 to 100 times background. In general, antibodies of the present invention bind antigens on the surface of target cells in the presence of effector cells (such as natural killer cells or macrophages). Fc receptors on effector cells recognize bound antibodies.

An antibody immunologically reactive with a particular antigen can be generated by recombinant methods such as selection of libraries of recombinant antibodies in phage or similar vectors, or by immunizing an animal with the antigen or with DNA encoding the antigen. Methods of preparing polyclonal antibodies are known to the skilled artisan. The antibodies may, alternatively, be monoclonal antibodies. Monoclonal antibodies may be prepared using hybridoma methods. In a hybridoma method, an appropriate host animal is typically immunized with an immunizing agent to elicit lymphocytes that produce or are capable of producing antibodies that will specifically bind to the immunizing agent. Alternatively, the lymphocytes may be immunized in vitro. The lymphocytes are then fused with an immortalized cell line using a suitable fusing agent, such as polyethylene glycol, to form a hybridoma cell.

Human antibodies can be produced using various techniques known in the art, including phage display libraries. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire.

Antibodies also exist as a number of well-characterized fragments produced by digestion with various peptidases. Thus pepsin digests an antibody below the disulfide linkages in the hinge region to produce F(ab')$_2$, a dimer of Fab which itself is a light chain joined to $V_H$-$C_{H1}$ by a disulfide bond. The F(ab')$_2$ may be reduced under mild conditions to break the disulfide linkage in the hinge region, thereby converting the F(ab')$_2$ dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries.

A "humanized antibody" is an immunoglobulin molecule which contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin.

Antibodies of interest may be tested for their ability to induce ADCC (antibody-dependent cellular cytotoxicity) or ADCP (antibody dependent cellular phagocytosis). Antibody-associated ADCC activity can be monitored and quantified through detection of either the release of label or lactate dehydrogenase from the lysed cells, or detection of reduced target cell viability (e.g. annexin assay). Assays for apoptosis may be performed by terminal deoxynucleotidyl transferase-mediated digoxigenin-11-dUTP nick end labeling (TUNEL) assay (Lazebnik et al., Nature: 371, 346 (1994). Cytotoxicity may also be detected directly by detection kits known in the art, such as Cytotoxicity Detection Kit from Roche Applied Science (Indianapolis, Ind.).

A "patient" for the purposes of the present invention includes both humans and other animals, particularly mammals, including pet and laboratory animals, e.g. mice, rats, rabbits, etc. Thus the methods are applicable to both human therapy and veterinary applications. In one embodiment the patient is a mammal, preferably a primate. In other embodiments the patient is human.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer. Subjects may be human, but also include other mammals, particularly those mammals useful as laboratory models for human disease, e.g. mouse, rat, etc.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. Cells of interest for detection, analysis, or treatment in the present application include precancerous (e.g., benign), malignant, pre-metastatic, metastatic, and non-metastatic cells. Cancers of virtually every tissue are known. The phrase "cancer burden" refers to the quantum of cancer cells or cancer volume in a subject. Reducing cancer burden accordingly refers to reducing the number of cancer cells or the cancer volume in a subject. The term "cancer cell" as used herein refers to any cell that is a cancer cell or is derived from a cancer cell e.g. clone of a cancer cell. Many types of cancers are known to those of skill in the art, including solid tumors such as carcinomas, sarcomas, glioblastomas, melanomas, lymphomas, myelomas, etc., and circulating cancers such as leukemias. Examples of cancer include but are not limited to, ovarian cancer, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor. Metastasis can also be defined as several steps of a process, such as the departure of cancer cells from an original tumor site, and migration and/or invasion of cancer cells to other parts of the body.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample comprising cancer cells from a patient. A biological sample comprising a cancer cell from a patient can also include non-cancerous cells.

The term "diagnosis" is used herein to refer to the identification of a molecular or pathological state, disease or condition, such as the identification of a molecular subtype of breast cancer, prostate cancer, or other type of cancer.

The term "prognosis" is used herein to refer to the prediction of the likelihood of cancer-attributable death or progression, including recurrence, metastatic spread, and drug resistance, of a neoplastic disease, such as ovarian cancer. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

As used herein, the terms "treatment," "treating," and the like, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

Treating may refer to any indicia of success in the treatment or amelioration or prevention of an cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with cancer or other diseases. The term "therapeutic effect" refers to the reduction, elimination, or prevention of the disease, symptoms of the disease, or side effects of the disease in the subject.

"In combination with", "combination therapy" and "combination products" refer, in certain embodiments, to the concurrent administration to a patient of a first therapeutic and the compounds as used herein. When administered in combination, each component can be administered at the same time or sequentially in any order at different points in time. Thus, each component can be administered separately but sufficiently closely in time so as to provide the desired therapeutic effect.

"Concomitant administration" of a cancer therapeutic drug, ESA or tumor-directed antibody with a pharmaceutical composition of the present invention means administration with the high affinity CD47 reagent at such time that both the drug, ESA or antibody and the composition of the present invention will have a therapeutic effect. Such concomitant administration may involve concurrent (i.e. at the same time), prior, or subsequent administration of the drug, ESA or antibody with respect to the administration of a compound of the invention. A person of ordinary skill in the art would have no difficulty determining the appropriate timing, sequence and dosages of administration for particular drugs and compositions of the present invention.

As used herein, endpoints for treatment will be given a meaning as known in the art and as used by the Food and Drug Administration.

Overall survival is defined as the time from randomization until death from any cause, and is measured in the intent-to-treat population. Survival is considered the most reliable cancer endpoint, and when studies can be conducted to adequately assess survival, it is usually the preferred endpoint. This endpoint is precise and easy to measure, documented by the date of death. Bias is not a factor in endpoint measurement. Survival improvement should be analyzed as a risk-benefit analysis to assess clinical benefit. Overall survival can be evaluated in randomized controlled studies. Demonstration of a statistically significant improvement in overall survival can be considered to be clinically significant if the toxicity profile is acceptable, and has often supported new drug approval. A benefit of the methods of the invention can include increased overall survival of patients.

Endpoints that are based on tumor assessments include DFS, ORR, TTP, PFS, and time-to-treatment failure (TTF). The collection and analysis of data on these time-dependent endpoints are based on indirect assessments, calculations, and estimates (e.g., tumor measurements). Disease-Free Survival (DFS) is defined as the time from randomization until recurrence of tumor or death from any cause. The most frequent use of this endpoint is in the adjuvant setting after definitive surgery or radiotherapy. DFS also can be an important endpoint when a large percentage of patients achieve complete responses with chemotherapy.

Objective Response Rate. ORR is defined as the proportion of patients with tumor size reduction of a predefined amount and for a minimum time period. Response duration usually is measured from the time of initial response until documented tumor progression. Generally, the FDA has defined ORR as the sum of partial responses plus complete responses. When defined in this manner, ORR is a direct measure of drug antitumor activity, which can be evaluated in a single-arm study.

Time to Progression and Progression-Free Survival. TTP and PFS have served as primary endpoints for drug approval. TTP is defined as the time from randomization until objective tumor progression; TTP does not include deaths. PFS is defined as the time from randomization until objective tumor progression or death. The precise definition of tumor progression is important and should be carefully detailed in the protocol.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

METHODS OF USE

Methods are provided for treating or reducing primary or metastatic cancer, specifically including EGFR-expressing epithelial cancers, e.g. adenocarcinomas, colorectal carcinomas; squamous cell carcinomas; basal cell carcinomas; ovarian cancer, pancreatic cancer, breast cancer, NSCLC; EGFR expressing gliomas; etc., in a regimen comprising contacting the targeted cells with a combination of agents that (i) an agent that blockades CD47 activity; and (ii) an antibody that specifically binds to EGFR. Such methods include administering to a subject in need of treatment a therapeutically effective amount or an effective dose of the combined agents of the invention, including without limitation combinations of the reagent with a chemotherapeutic drug, radiation therapy, or an ESA.

Effective doses of the combined agents of the present invention for the treatment of cancer, vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g. companion animals such as dogs, cats, horses, etc., laboratory mammals such as rabbits, mice, rats, etc., and the like. Treatment dosages can be titrated to optimize safety and efficacy.

In some embodiments, the therapeutic dosage of each agent may range from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

In prophylactic applications, a relatively low dosage may be administered at relatively infrequent intervals over a long period of time. Some patients continue to receive treatment for the rest of their lives. In other therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

In still other embodiments, methods of the present invention include treating, reducing or preventing tumor growth, tumor metastasis or tumor invasion of cancers including carcinomas, gliomas, etc. For prophylactic applications, pharmaceutical compositions or medicaments are administered to a patient susceptible to, or otherwise at risk of disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

Compositions for the treatment of cancer can be administered by parenteral, topical, intravenous, intratumoral, oral, subcutaneous, intraarterial, intracranial, intraperitoneal, intranasal or intramuscular means. A typical route of administration is intravenous or intratumoral, although other routes can be equally effective.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the combined agents described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that compositions of the invention when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The compositions for administration will commonly comprise an antibody or other ablative agent dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

Also within the scope of the invention are kits comprising the compositions (e.g., anti-EGFR antibodies; anti-CD47 agents, and formulations thereof) of the invention and instructions for use. The kit can further contain a least one additional reagent, e.g. a chemotherapeutic drug, ESA, etc. Kits typically include a label indicating the intended use of the contents of the kit. The term label includes any writing, or recorded material supplied on or with the kit, or which otherwise accompanies the kit.

The compositions can be administered for therapeutic treatment. Compositions are administered to a patient in an amount sufficient to substantially ablate targeted cells, as described above. An amount adequate to accomplish this is defined as a "therapeutically effective dose.", which may provide for an improvement in overall survival rates. Single or multiple administrations of the compositions may be administered depending on the dosage and frequency as required and tolerated by the patient. The particular dose required for a treatment will depend upon the medical condition and history of the mammal, as well as other factors such as age, weight, gender, administration route, efficiency, etc.

EXPERIMENTAL

Example 1

Treatment of Colorectal Cancer with Combined CD47 Blockade and Anti-EGFR

All methods have been described previously, which references are herein specifically incorporated by reference:
Dalerba, P., S. J. Dylla, Et Al. (2007). "Phenotypic Characterization Of Human Colorectal Cancer Stem Cells." Proc Natl Acad Sci USA 104(24): 10158-10163.
Weiskopf, K., A. M. Ring, Et Al. (2013). "Engineered Sirp alpha Variants As Immunotherapeutic Adjuvants To Anticancer Antibodies." Science 341(6141): 88-91.
Willingham, S. B., J. P. Volkmer, Et Al. (2012). "The Cd47-Signal Regulatory Protein Alpha (Sirpa) Interaction Is A Therapeutic Target For Human Solid Tumors." Proc Natl Acad Sci USA 109(17): 6662-6667.
Epigentic and genetic features of 24 colon cancer cell lines, Ahmed et al., Oncogenesis, 2013

Cancer Cells. DLD1 cells (ATCC), HT29 cells (ATCC), SW620 cells (ATCC), SW48 cells (ATCC), LS174T cells (ATCC), HCT116 cells (ATCC), and CACO-2 cells (ATCC) were cultured in RPMI (ThermoFisher S.) (DLD1), EMEM (ThermoFisher S.) (CACO-2, LS174T), McCoy's 5A (ThermoFisher S.) (HT29, HCT116), or Leibovitz's L-15 (ThermoFisher S.) (SW48, SW 620) supplemented with 10% fetal bovine serum (Omega Scientific), 100 U/mL penicillin and 100 µg/mL streptomycin (ThermoFisher S.). GFP-luciferase+ DLD1 cell line was generated by transduction using a pCDH-CMV-MCS-EF1 puro HIV-based lentiviral vector (Systems Biosciences) engineered to express an eGFP-luciferase2 (pgl4) fusion protein. Stable lines were created by sorting for GFP expression on FACSAria II cell sorters (BD Biosciences). UM8 patient xenograft cancer cells (adenocarcinoma, sigmoid colon, T3N0Mx) have been obtained from obtained from P. Dalerba, who established and characterized these previously (Dalerba, P., S. J. Dylla, Et Al. (2007). "Phenotypic Characterization Of Human Colorectal Cancer Stem Cells." Proc Natl Acad Sci USA 104(24): 10158-10163). Tumor cells were transduced overnight with lentivirus in culture media containing 6 µg/mL polybrene. The following day, cells were washed repeatedly to remove polybrene and extracellular lentivirus. Transduced (GFP+) cells were later isolated from xenograft tumors by FACS.

In Vitro Phagocytosis Assay. Peripheral blood mononuclear cells were enriched by density gradient centrifugation and monocytes were purified with anti-CD14 microbeads (Miltenyi) and differentiated to macrophages by culture for 7-10 days in IMDM+GlutaMax (Invitrogen) supplemented with 10% AB-Human Serum (Invitrogen) and 100 U/mL penicillin and 100 µg/mL streptomycin (Invitrogen). Phagocytosis assays were performed by co-culture of 50,000 macrophages with 100,000 GFP+ tumor cells for 2 hours, then analyzed using an LSRFortessa cell analyzer with high throughput sampler (BD Biosciences). Antibodies used for treatment included: IgG4 isotype control, anti-CD47—clone Hu5F9-G4 (Stanford), and anti-EGFR cetuximab (Bristoll-Myers Squibb). Macrophages were identified by flow cytometry using anti-CD206 antibody. Dead cells were excluded from the analysis by staining with DAPI (Sigma). Phagocytosis was evaluated as the percentage of GFP+ macrophages and was normalized to the maximal response by each independent donor against each cell line.

Mice. 6-8 week old NSG (NOD.Cg-Prkdcscid Il2rgtm1Wjl/SzJ) mice were used. The Stanford colony of these mice was founded by mice purchased from Jackson Labs (Stock 005557).

In Vivo Imaging. Bioluminescent imaging was performed on an IVIS Spectrum (Caliper Life Science) and quantified using Living Image 4.0 software. D-luciferin (firefly) potassium salt (Biosynth) solution was prepared by dissolving 1 g in 60 mL PBS. Mice were injected IP with 200 µL luciferin solution. Total flux (photons/second) values were obtained from the anatomic region of tumor engraftment twenty minutes after luciferin injection.

Ex Vivo Detection of Metastases. Metastases to lungs and lymph nodes were visualized by detecting GFP+ cancer cells in lungs and lymph nodes with a M205 FA fluorescent dissecting microscope (Leica) fitted with a DFC 500 camera (Leica).

Xenograft Tumor Models. 50,000 GFP-luciferase+ DLD1 cells or 240,000 GFP-luciferase+ UM8 cells were transplanted with 50% Matrigel (BD) onto the back of NSG mice. In both models, treatment was initiated upon confirmation of tumor engraftment by bioluminescence imaging and continued as indicated. For all treatments, antibodies where administered by intraperitoneal injection (100 µl) as follows: PBS and Hu5F9-G4 (250 µg) every other day; cetuximab (120 µg) and panitumumab (120 µg) once weekly. Tumor growth was monitored by bioluminescence imaging. For the DLD1 model mice where analyzed for the presence of lung and lymph node metastases after completion of the indicated treatment period by detection of GFP+ cancer cells in lungs and lymph nodes with a fluorescent dissecting microscope.

Example 2

A Phase 1 b/2 Trial of Hu5F9-G4 in Combination with Cetuximab in Solid Tumor and Advanced Metastatic Colorectal Cancer Patients CRC is the third leading cause of cancer-related deaths in the US in which 20% of patients have metastatic disease. Treatment options are limited for metastatic CRC patients after failing frontline treatment. Thus, novel and effective therapies are needed. Hu5F9-G4 is a first-in-class monoclonal antibody targeting CD47, an anti-phagocytic signal expressed on cancer stem cells, with anti-tumor efficacy achieved through depleting CRC and cancer stem cells by macrophage and T cell induced elimination. Pre-clinical studies have demonstrated dramatic synergistic anti-tumor effect when Hu5F9-G4 is combined with the clinically approved anti-EGFR monoclonal antibody cetuximab. This synergistic efficacy extends to KRAS mutant patients: which comprise up to 40% of all CRC patients, have limited therapeutic options, and whereby single agent cetuximab in not FDA approved due to lack of antitumor activity. Thus, Hu5F9-G4 can rescue and potentiate cetuximab activity in this population with high unmet medical need. These pre-clinical data form the basis to test clinical anti-tumor proof of concept in the proposed Phase 1 b/2 clinical trial in relapsed/refractory KRAS mutant metastatic CRC and KRAS wildtype metastatic patients refractory to anti-EGFR therapies.

Metastatic colorectal adenocarcinoma is a tumor with high relapse rate and poor long-term survival. The EGFR targeting antibodies such as cetuximab and panitumumab have significantly improved prognosis in KRAS wildtype patients. However, patients with KRAS mutations, which comprise approximately 40-50% of colorectal cancers, do not respond to anti-EGFR antibody therapies. Thus, additional therapies are needed to address this high unmet medical need.

Hu5F9-G4 is a monoclonal antibody that targets CD47, an anti-phagocytic cell surface protein. Pre-clinical studies have demonstrated that blockade of CD47 signaling through this antibody eliminates human tumor cells including colorectal cancer, through facilitating phagocytosis by macrophages. Additional pre-clinical studies demonstrate that anti-CD47 antibodies can synergize with Fc receptor-activating anti-cancer antibodies including cetuximab and panitumumab. Combination therapy with Hu59-G4 and anti-EGFR antibodies has led to significant responses in both RAS wildtype and mutant in vivo models compared to either agent alone.

The combination of Hu5F9-G4 and cetuximab is tested for safe tolerance in solid tumor patients, including colorectal cancer. A Phase 1 b/2 trial establishes the safety and tolerability and optimal dosing strategy of Hu5F9-G4 in combination with cetuximab administered intravenously to advanced solid tumor patients and advanced metastatic colorectal cancer patients. In the Phase 1 b portion of the trial, the combination is evaluated in an all comer solid tumor population with an emphasis on treating patients with CRC, head & neck, breast, pancreatic, and ovarian cancer.

Patients at a starting cetuximab dose of 300 mg/m$^2$ followed by weekly doses of 200 mg/m$^2$ are 25% and 20% reductions, respectively, from the full single agent doses of cetuximab. The initial dose of Hu5F9-G4 consists of a priming dose of 1 mg/kg followed by weekly maintenance doses of 10 mg/kg. In the next cohort, cetuximab is escalated to the full single agent dose of 400 mg/m$^2$ followed by weekly 250 mg/m$^2$. Subsequent dose cohorts escalate the dose of Hu5F9-G4 to the full single agent dose including a loading dose strategy in the combination. The maximum doses evaluated do not exceed the single agent recommended dose and schedule for each individual antibody. In the Phase 2 part of the trial, preliminary antitumor activity is investigated at the recommended Phase 2 dose of the combination in selected populations of CRC patients.

Key Inclusion Criteria
1. Adults ≥18 years old
2. Histological Diagnosis
a. Phase 1 b only: Histologically or cytologically confirmed advanced solid malignancy with an emphasis on CRC, Head & Neck, breast, pancreatic and ovarian cancers who have been treated with at least one regimen of prior systemic therapy, or who refuse systemic therapy, and for which there is no curative therapy available;
b. Phase 2 RAS Mutant CRC: Histologically confirmed advanced/metastatic RAS mutant CRC who have progressed or are ineligible for both irinotecan- and oxaliplatin-based chemotherapy OR
c. Phase 2 RAS Wild-Type CRC: Histologically confirmed advanced/metastatic RAS wildtype CRC who have progressed or are ineligible for both irinotecan- and oxaliplatin-based chemotherapy and who are relapsed or refractory to at least 1 prior systemic therapy that included an anti-EGFR antibody, such as cetuximab, panitumumab or others
3. ECOG Score 0-2
4. For the Phase 2 part only: Disease that is measurable or assessable for response according to RECIST 1.1
5. Laboratory measurements, blood counts:
Hemoglobin ≥9.5 g/dL
ANC ≥1.0×10$^9$/mL
Platelets ≥75×10$^9$/mL
6. Laboratory measurements, hepatic function:
AST/ALT ≤5×ULN
Bilirubin ≤1.5×ULN or 3.0×ULN and primarily unconjugated if patient has a documented history of Gilbert's syndrome or a genetic equivalent
7. Laboratory measurements, renal function:
Serum creatinine ≤1.5λ ULN or if elevated, a calculated GFR ≤40 mL/min/1.73 m$^2$
8. Negative urine or serum pregnancy test within 30 days before administration of Hu5F9-G4 for women of childbearing potential
9. Females of childbearing potential must be willing to use 2 effective methods of contraception during the study and continue for 6 months after the last dose of study drug
10. Males must be willing to use 1 highly effective method of contraception during the study and continue for 6 months after the last dose of study drug, if the partner is a female of childbearing potential
11. Subject has provided informed consent
12. Must be willing and able to comply with the clinic visits and procedures outlined in the study protocol
13. Phase 2 only: Willing to consent to 1 mandatory pre-treatment and 1 on-treatment tumor biopsy, unless determined to not be feasible by the Investigator (reasons include, but are not limited to, lack of accessible tumor tissue to biopsy and patient safety issues)

Exclusion Criteria
1. Patients with active brain metastases (patients with stable treated CNS lesions who are off corticosteroid and radiation therapy for at least 3 weeks are not considered active)
2. Prior anticancer therapy including chemotherapy, hormonal therapy, or investigational agents within 2 weeks or within at least 4 half-lives prior to Hu5F9-G4 dosing (up to a maximum of 4 weeks), whichever is longer. Localized non-CNS radiotherapy, pre-existing hormonal therapy with LHRH agonists, low dose steroids (oral prednisone or equivalent ≤20 mg per day), and treatment with bisphosphonates and RANKL inhibitors are not criteria for exclusion.
3. Prior treatment with CD47 or SIRPα-targeting agents
4. Known active or chronic hepatitis B or C infection or HIV
5. RBC transfusion dependence, defined as requiring more than 2 units of RBC transfusions during the 4-week period prior to the first dose of Hu5F9-G4. RBC transfusions are permitted during screening and prior to enrollment to meet the hemoglobin inclusion criteria.
6. History of hemolytic anemia or Evans syndrome in the last 3 months
7. Phase 2 only: Second malignancy, except treated basal cell or localized squamous skin carcinomas, or other malignancy that for which treatment was completed at least 3 years ago and for which there is no evidence of recurrence
8. Significant medical diseases or conditions, as assessed by the Investigators and Sponsor, that would substantially increase the risk/benefit ratio of participating in the study. This includes, but is not limited to, acute myocardial infarction within the last 6 months, unstable angina, uncontrolled diabetes mellitus, significant active infections, severely immunocompromised state, and congestive heart failure NYHA Class II-IV 9. History of psychiatric illness or substance abuse likely to interfere with ability to comply with protocol requirements or give informed consent
10. Pregnancy or active breast feeding
11. Positive Direct Antiglobulin Test (DAT)

The objective response rate (ORR) of Hu5F9-G4 in combination with cetuximab in patients with RAS mutant and RAS wild-type CRC is determined. Secondary objectives include evaluation of the pharmacokinetic (PK) profile of Hu5F9-G4 in combination with cetuximab. In Phase 2 secondary parameters of efficacy are evaluated, such as duration of response (DOR), progression free survival (PFS), time to tumor progression, and overall survival for patients with RAS mutant and RAS wild-type CRC treated with Hu5F9-G4 in combination with cetuximab.

Pharmacodynamic (PD) and predictive markers including immune cell subset frequencies and tumor penetration of Hu5F9-G4 in combination with cetuximab are assessed. Efficacy in molecular subtypes of CRC are assessed.

Hu5F9-G4 is a humanized monoclonal antibody against CD47 and cetuximab is a chimeric monoclonal antibody against EGFR. Both drugs are administered intravenously. In Cycle 1, a priming dose of Hu5F9 is administered on Day 1 and then weekly cetuximab and Hu5F9 are administered with each cycle being 28 days. The first loading dose of cetuximab is administered on day 8, followed by the first maintenance dose of Hu5F9-G4 on day 9 in Cycle 1 but all subsequent doses of the combination are administered on the same starting on day 15. On days of simultaneous administration, cetuximab is infused first prior to Hu5F9-G4 administration. This schedule is illustrated in the table below:

| Dose Co-hort | Drug/Dose (IV) | Dose Schedule (Day per 28-day Cycle) | |
|---|---|---|---|
| | | Cycle 1 | Cycle 2+ |
| 1 | Hu5F9-G4 1 mg/kg (prime) | Day 1 | — |
| | Hu5F9-G4 10 mg/kg (maintenance) | Day 9, 15, 22 | Day 1, 8, 15, 22 |
| | Cetuximab 300 mg/m² (load) | Day 8 | |
| | Cetuximab 200 mg/m² (maintenance) | Day 15, 22 | Day 1, 8, 15, 22 |
| 2 | Hu5F9-G4 1 mg/kg (prime) | Day 1 | — |
| | Hu5F9-G4 10 mg/kg (maintenance) | Day 9, 15, 22 | Day 1, 8, 15, 22 |
| | Cetuximab 400 mg/m² (load) | Day 8 | |
| | Cetuximab 250 mg/m² (maintenance) | Day 15, 22 | Day 1, 8, 15, 22 |
| 3 | Hu5F9-G4 1 mg/kg (prime) | Day 1 | — |
| | Hu5F9-G4 20 mg/kg (maintenance) | Day 9, 15, 22 | Day 1, 8, 15, 22 |
| | Cetuximab 400 mg/m² (load) | Day 8 | |
| | Cetuximab 250 mg m² (maintenance) | Day 15, 22 | Day 1, 8, 15, 22 |
| 4 [a] | Hu5F9-G4 1 mg/kg (prime) | Day 1 | — |
| | Hu5F9-G4 20 mg/kg (load) | Day 9 and 11 | — |
| | Hu5F9-G4 10-20 mg/kg (maintenance) | Day 15, 22 | Day 1, 8, 15, 22 |
| | Cetuximab 400 mg/m² (load) | Day 8 | — |
| | Cetuximab 250 mg m² (maintenance) | Day 15, 22 | Day 1, 8, 15, 22 |

[a] Potential loading dose cohort may be added if deemed necessary by the CTSC.

For Part A of the study, patients are treated for 8 weeks with Hu5F9-G4 and cetuximab. DLT safety evaluation used for determination of MTD will occur within the first 4 weeks. A response assessment (according to modified RECIST criteria) will occur every 2 cycles. Response assessment will occur every two cycles from start of treatment until disease progression.

Phase 2 includes two arms, one comprising patients with RAS mutant CRC and the other comprising patients with RAS wild type CRC. For the first stage of the Simon two-stage design, patients are treated for 8 weeks and then response rate assessed. Objective response rate (ORR) (CR+PR) is determined according to modified RECIST 1.1 criteria. Response assessment will occur every two cycles from start of treatment until disease progression. A maximum of 88 patients (44 patients per arm) are enrolled in Phase 2. Sample size for Phase 2 was based on a Simon's two stage minimax design for each cohort using a one sided alpha level of 0.10 and a power of 0.80 based on a null hypothesis of 5% response rate compared to an alternative hypothesis of 15% for each cohort.

Phase 1b total: 15 to 24 patients. Phase 2: Up to 88 patients total (44 in each cohort) In each cohort: Simon Two-Stage design, Stage 1=29 pts; Stage 2=15 additional patients Each publication cited in this specification is hereby incorporated by reference in its entirety for all purposes.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

What is claimed is:

1. A method of treating an individual human for immunodepletion of metastatic EGFR-expressing colorectal carcinoma cells in which an activating mutation in one or more of KRAS, NRAS and BRAF is present, the method comprising:
administering to the individual:
a dose of 1 mg/kg of an antibody that binds to CD47 and blockades CD47 activity; and after a period of time effective for an increase in reticulocyte production administering (i) an antibody that binds to CD47 and blockades CD47 activity; and (ii) an antibody that specifically binds to epidermal growth factor receptor; both in a dose effective to increase immunodepletion of the targeted EGFR-expressing colorectal carcinoma cells.

2. The method of claim 1, further comprising testing the EGFR-expressing cancer cells for the presence of an activating mutation in one or more of KRAS, NRAS and BRAF; and selecting for treatment cancer cells in which an activating mutation is present.

3. The method of claim 1, wherein the antibody that specifically binds to EGFR is an antagonist of EGFR signaling pathway.

4. The method of claim 1, wherein the antibody that specifically binds to EGFR is a non-antagonist of EGFR signaling pathway.

5. The method of claim 1, wherein depletion of the target cells is enhanced relative to the depletion observed with a monotherapy of (i) an antibody that blockades CD47 activity; or (ii) an anti-EGFR antibody.

6. The method of claim 1, wherein the anti-CD47 antibody comprises an IgG4 Fc region.

7. The method of claim 6, wherein the anti-CD47 antibody comprises a variable heavy (VH) region containing the VH complementarity regions, CDR1, CDR2 and CDR3, respectively set forth in SEQ ID NO:1, 2 and 3; and a variable light (VL) region containing the VL complementary regions, CDR1, CDR2 and CDR3, respectively set forth in in SEQ ID NO:4, 5, 6.

8. The method of claim 1, further comprising administering an effective dose of an erythropoietin stimulating agent to increase patient hematocrit.

\* \* \* \* \*

SEQUENCE LISTING

<160> NUMBER OF SEQ ID NOS: 6

<210> SEQ ID NO 1
<211> LENGTH: 5
<212> TYPE: PRT
<213> ORGANISM: Mus musculus

```
<400> SEQUENCE: 1

Asn Tyr Asn Met His
1               5

<210> SEQ ID NO 2
<211> LENGTH: 17
<212> TYPE: PRT
<213> ORGANISM: Mus musculus

<400> SEQUENCE: 2

Thr Ile Tyr Pro Gly Asn Asp Asp Thr Ser Tyr Asn Gln Lys Phe Lys
1               5                   10                  15

Asp

<210> SEQ ID NO 3
<211> LENGTH: 8
<212> TYPE: PRT
<213> ORGANISM: Mus musculus

<400> SEQUENCE: 3

Gly Gly Tyr Arg Ala Met Asp Tyr
1               5

<210> SEQ ID NO 4
<211> LENGTH: 16
<212> TYPE: PRT
<213> ORGANISM: Mus musculus

<400> SEQUENCE: 4

Arg Ser Ser Gln Ser Ile Val Tyr Ser Asn Gly Asn Thr Tyr Leu Gly
1               5                   10                  15

<210> SEQ ID NO 5
<211> LENGTH: 7
<212> TYPE: PRT
<213> ORGANISM: Mus musculus

<400> SEQUENCE: 5

Lys Val Ser Asn Arg Phe Ser
1               5

<210> SEQ ID NO 6
<211> LENGTH: 9
<212> TYPE: PRT
<213> ORGANISM: Mus musculus

<400> SEQUENCE: 6

Phe Gln Gly Ser His Val Pro Tyr Thr
1               5
```